(12) United States Patent
Ballard et al.

(10) Patent No.: US 9,414,859 B2
(45) Date of Patent: Aug. 16, 2016

(54) SURGICAL ROD MEASURING SYSTEM AND METHOD

(71) Applicant: Warsaw Orthopedic, Inc., Warsaw, IN (US)

(72) Inventors: Rodney Ballard, Lakeland, TN (US); David Mire, Cordova, TN (US); William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 176 days.

(21) Appl. No.: 13/866,536

(22) Filed: Apr. 19, 2013

(65) Prior Publication Data

US 2014/0316420 A1 Oct. 23, 2014

(51) Int. Cl.
*A61B 17/70* (2006.01)
*A61B 17/88* (2006.01)
*A61B 17/56* (2006.01)
*A61F 2/46* (2006.01)

(52) U.S. Cl.
CPC ......... *A61B 17/7002* (2013.01); *A61B 17/8863* (2013.01); *A61B 17/7013* (2013.01); *A61B 17/7074* (2013.01); *A61B 17/7083* (2013.01); *A61B 2017/568* (2013.01); *A61B 2034/104* (2016.02); *A61B 2034/2048* (2016.02); *A61F 2/4657* (2013.01)

(58) Field of Classification Search
CPC ........... A61B 17/7013; A61B 17/7074; A61B 17/7083; A61B 17/8863; A61B 19/46; A61B 19/50; A61B 2017/568; A61B 2019/461; A61B 2019/502; A61B 2019/507; A61B 2019/508; A61B 2019/5268; A61F 2/4657
See application file for complete search history.

(56) References Cited

U.S. PATENT DOCUMENTS

| 6,226,548 | B1 * | 5/2001 | Foley et al. | 600/426 |
| 2004/0158260 | A1 * | 8/2004 | Blau et al. | 606/108 |
| 2005/0085714 | A1 * | 4/2005 | Foley et al. | 600/424 |
| 2008/0082119 | A1 * | 4/2008 | Vitullo | 606/192 |
| 2009/0254097 | A1 * | 10/2009 | Isaacs | 606/130 |
| 2009/0254326 | A1 * | 10/2009 | Isaacs | 703/11 |
| 2010/0100081 | A1 * | 4/2010 | Tuma et al. | 606/1 |
| 2012/0035507 | A1 * | 2/2012 | George et al. | 600/587 |
| 2013/0268007 | A1 * | 10/2013 | Rezach et al. | 606/279 |
| 2013/0345757 | A1 * | 12/2013 | Stad | 606/279 |
| 2014/0081121 | A1 * | 3/2014 | Wilhelm et al. | 600/409 |
| 2014/0228670 | A1 * | 8/2014 | Justis et al. | 600/409 |

* cited by examiner

*Primary Examiner* — Kevin T Truong
*Assistant Examiner* — Tracy Kamikawa (57) ABSTRACT

A system and method for measuring a surgical rod are disclosed. The system includes a processor, a probe in communication with the processor and configured to trace along a surface of the implant, a tracking system in communication with the processor and the probe for generating first data representing at least one of linear and rotational movement of the probe during a first trace along the surface of the implant, wherein the processor is configured to receive the first data and generate a first graphical representation of the implant based on the first data, and a display in communication with said processor for displaying the graphical representation of the implant based on the first data. Various methods are also disclosed.

19 Claims, 10 Drawing Sheets

SURGICAL ROD MEASURING SYSTEM AND METHOD

TECHNICAL FIELD

The present disclosure generally relates to medical devices, systems and methods for the treatment of musculoskeletal disorders, and more particularly to systems and methods for determining geometries of a surgical rod, and in particular a spinal rod, to provide stabilization of vertebrae.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatments of these spinal disorders include discectomy, laminectomy, fusion and implantable prosthetics. During surgical treatment, one or more rods may be attached via fasteners to the exterior of two or more vertebral members in a vertebral fixation system.

Normally when a rod is to be positioned within a fixation system, the rod requires bending and shaping to conform to precise curvature of a spine of a patient. This curvature can require bending of the rod in the sagittal, coronal and/or transverse planes of the patient. Surgeons typically predetermine the required geometries of the spine of the patient and then shape and bend a rod based on visual estimates. The shaped rod is then placed into bone anchors of the fixation system in the patient and the surgeon readjusts the shape and bends of the rod in situ based again on visual estimates in an attempt to best match the required geometries. This disclosure describes an improvement over these prior art technologies.

SUMMARY

Accordingly, a system for measuring an implant is provided. The system includes a processor, a probe in communication with the processor and configured to trace along a surface of the implant, a tracking system in communication with the processor and the probe for generating first data representing at least one of linear and rotational movement of the probe during a first trace along the surface of the implant, wherein the processor is configured to receive the first data and generate a first graphical representation of the implant based on the first data, and a display in communication with said processor for displaying the graphical representation of the implant based on the first data.

In one embodiment, a method for measuring an implant includes moving a probe along a surface of an implant prior to positioning the implant within a patient, tracking movement of the probe to obtain first data representing the implant, storing the first data in a memory, and displaying a first image representing the implant based on the first data.

In one embodiment, a method for measuring a surgical rod includes implanting at least one bone fixation element into a patient, bending the rod prior to positioning the rod within the patient, moving a probe along a surface of the rod prior to positioning the implant within the patient, tracking movement of the probe to obtain first data representing the rod, storing the first data in a memory, displaying a first image representing the rod based on the first data, positioning the rod in the patient, connecting the rod to at least one bone screw, moving the probe along the surface of the rod, tracking movement of the probe to obtain second data of the rod within the patient, storing the second data in the memory, and displaying a second image representing the rod based on the second data.

BRIEF DESCRIPTION OF THE DRAWINGS

The present disclosure will become more readily apparent from the specific description accompanied by the following drawings, in which.

Like reference numerals indicate similar parts throughout the figures. It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

The exemplary embodiments of the system and method for measuring a surgical rod are discussed in terms of medical devices for the treatment of musculoskeletal disorders and more particularly, in terms of a spinal fixation system that provides stabilization for treating a vertebral column. It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is contemplated that the disclosed systems and methods may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. The following discussion includes a description of a surgical rod measuring system and related methods in accordance with the principles of the present disclosure. Alternate embodiments are also disclosed. Reference will now be made in detail to the exemplary embodiments of the present disclosure, which are illustrated in the accompanying figures.

The surgical rod measurement system may include any appropriate surgical tracking system. For example, the surgical rod measurement system may include an optical tracking system, an electromagnetic tracking system, and acoustic tracking system, an ultrasound tracking system, an active device tracking system or any other appropriate tracking systems or combinations thereof. Although the following discussion generally relates to the use of an optical and/or electromechanical tracking system, it will be understood that any appropriate tracking system may be used and the optical and/or electromechanical tracking system is described merely as an example. Exemplary electromagnetic tracking systems are set out in U.S. Pat. No. 6,493,573, issued Dec. 10, 2002, entitled "METHOD AND SYSTEM FOR NAVIGATING A CATHETER PROBE IN THE PRESENCE OF FIELD-INFLUENCING OBJECTS"; U.S. Pat. No. 5,592,939, issued Jan. 14, 1997, entitled "METHOD AND SYSTEM FOR NAVIGATING A CATHETER PROBE; U.S. Pat. No. 6,516,212, issued Feb. 4, 2003, entitled "THREE DIMENSIONAL MAPPING"; U.S. Pat. No. 6,522,907, issued Feb. 18, 2003, entitled "SURGICAL NAVIGATION"; each of which is incorporated herein by reference. Other tracking systems are also described in U.S. Pat. No. 7,835,778, issued Nov. 16, 2010, entitled "METHOD AND APPARATUS FOR SURGICAL NAVIGATION OF A MULTIPLE PIECE CONSTRUCT FOR IMPLEMENTATION"; U.S. Pat. No. 6,470,207, issued Oct. 22, 2002, entitled "NAVIGATIONAL GUIDANCE VIA COMPUTER-ASSISTED FLUOROSCOPIC IMAGING"; each of which is incorporated herein by reference.

In addition, although the tracking system disclosed herein uses a probe in wireless communication with a detector to determine position and rotation data of the rod, other configurations are contemplated. For example, a probe having an active internal guidance system that can include gyroscopes and/or accelerometers can be used to track the position and rotation of the probe during its operation and be in direct communication with the control computer or processor, without the need for the detector. A probe in this type of system can communicate positional and rotational information of the probe to the processor in either a wired or wireless configuration. In addition, since the tracking is relative to the rod itself no wider coordinate system is required. Systems and methods for measuring a surgical rod will now be described with respect to FIGS. 1-12.

Figure 1:
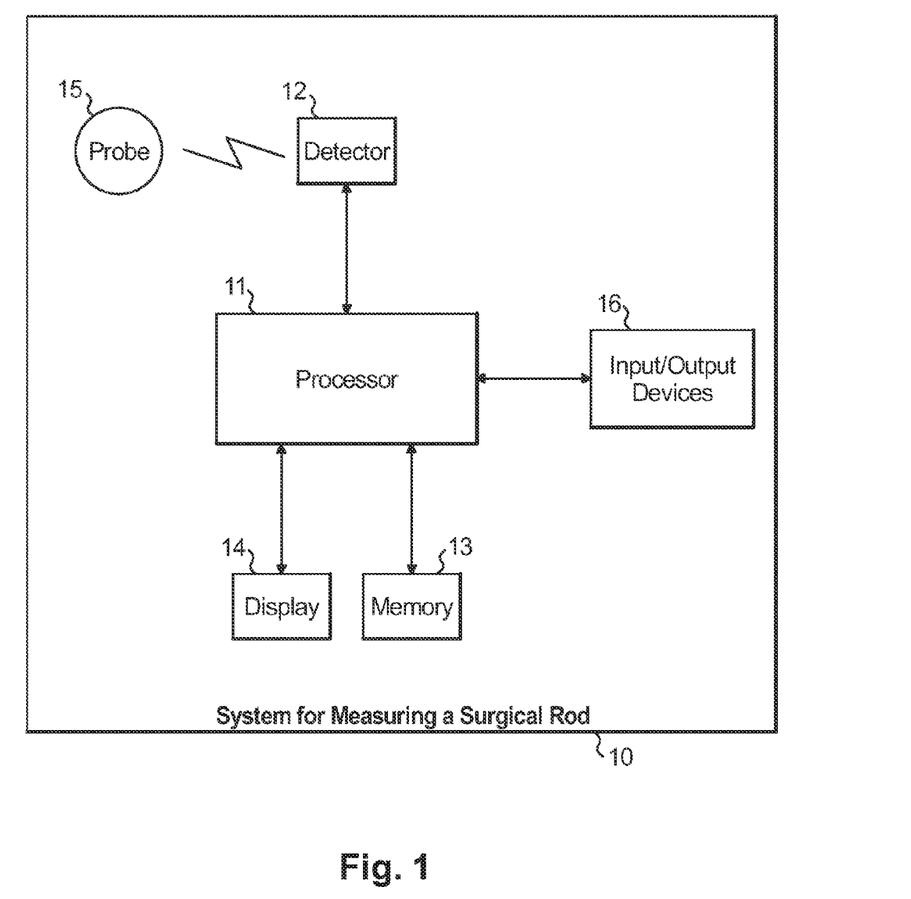
FIG. 1 is a block diagram of a system for measuring a surgical rod in accordance with the principles of the present disclosure.

In one embodiment, the system for measuring a surgical rod 10 includes a processor 11 for receiving positional and rotational data representative of movement of a probe 15 along a surgical rod 21. The data can be stored in a memory 13 in communication with the processor 11. Processor 11 receives the data and translates the data into a graphical representation 22 of the surgical rod 21. The graphical representation 22 can then be displayed on a display 14. At some point in time after the processor 11 receives the data, the processor 11 can determine angular geometries of the rod 21. The geometries can include angular measurements in any or all of the transverse, coronal and sagittal planes.

As stated above, a detector 12 in communication with the processor 11 can be used to track the position and rotation of the probe 15. The detector 12 may be operably located in any appropriate location such that the detector 12 is able to detect a tracking element 17 operably connected to the probe 15. For example, in an optical tracking system the tracking element may be one or more reflectors or light emitting diodes (LEDs). In an electromechanical system, the tracking element may be one or more radio transmitters to transmit an electromechanical signal.

It is contemplated that tracking element 17 can be disposed in or on the detector 12, probe 15, and/or rod 21 and be used to obtain rod geometries. For example, the tracking element 17 can be part of the detector 12 and obtain rod geometries, before, during and/or after surgery.

It is also contemplated that tracking element 17 can be in a rod bender (not shown), where the rod geometries can be obtained and transmitted to the processor 11 via a wired or wireless connection, for example, before, during and/or after surgery.

In a system wherein the probe contains active devices to determine movement as the tracking elements, e.g. gyroscopes and/or accelerators, the probe can contain its own processor and transmitter to receive electronic signals from the tracking elements and transmit the signals to the detector, which in this case can be a receiver. The transmission and reception can utilize radio frequency (RF) technology to transmit and receive the signals. Also, as stated above, a system using the active tracking elements can be hardwired to the processor and thus eliminate the need for the transmitter and receiver (i.e. detector).

The detector 12 may also be operable to detect other tracking elements located within the range of the detector 12. For example, the detector 12 may also be able to detect other probes (not shown), or detect a location of a rod equipped with a tracking element (not shown). As discussed herein, however, the tracking of the location of the rod 21 may not be necessary, but can be included based on the selected parameters for the tracking system 10, the procedure being performed, user preference, and other appropriate considerations. Nevertheless, if the location of the rod 21 is to be tracked, the tracking element 17 is generally affixed to the rod 21.

The tracking element can be used to trace the rod. The tracing of the rod does not need to be contiguous and can be started and stopped at various points or portions on the rod. This can be displayed as non-contiguous segments or can be interpolated and shown as one continuous rod. Alternatively, the rod may be held in front of the tracking system in at least one view whereby the tracking system will "see" the rod and store the location of the rod and display it on the screen. A retro-reflective surface such as retro-reflective tape or a marker may be applied to the rod to intensify the signal for the tracking. Yet another alternative of contact or noncontact measurement may be achieved by wrapping a coil around the bent rod.

Figure 4A:
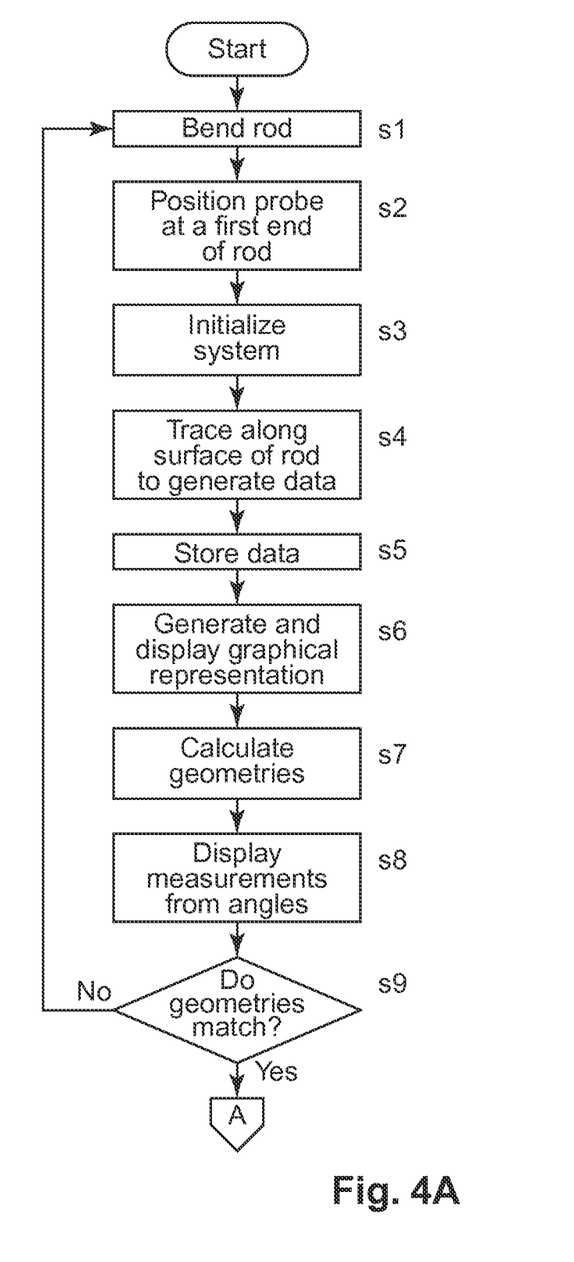
FIGS. 4A and 4B are a flow diagram illustrating a method in accordance with the principles of the present disclosure.
Figure 4B:
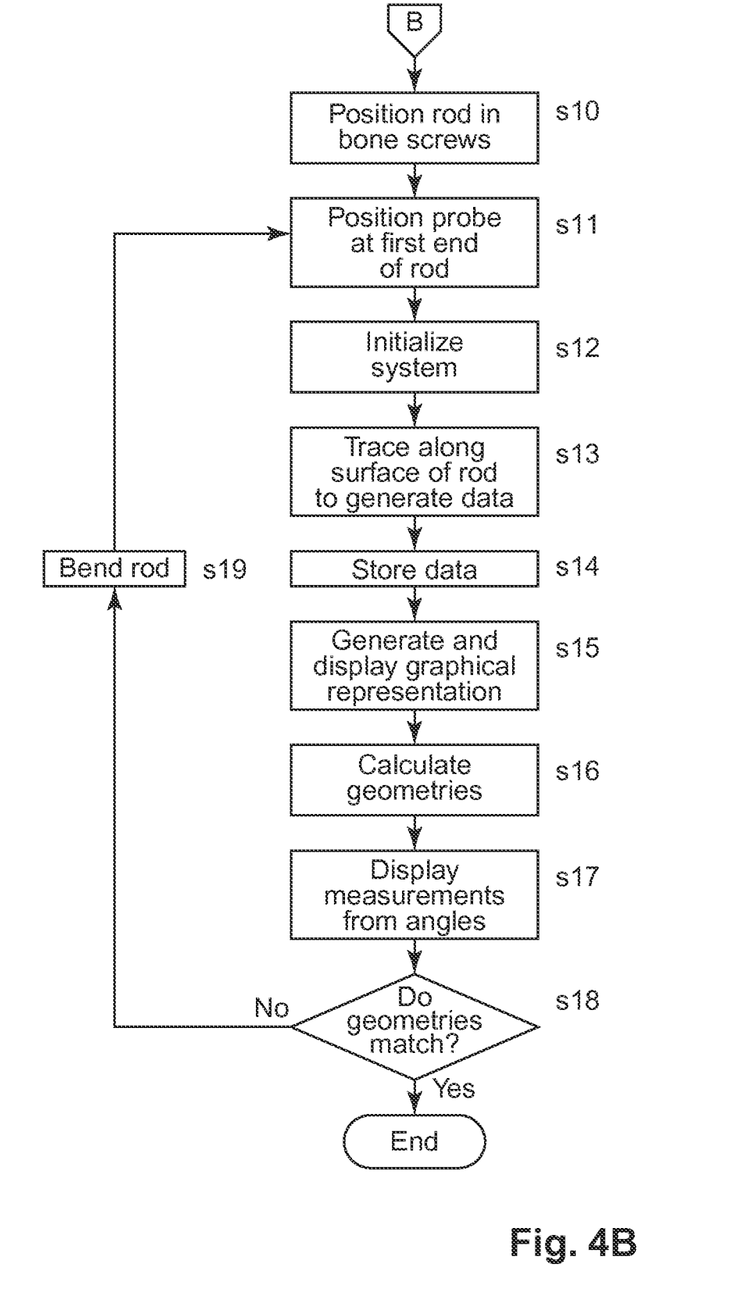
Figure 4C:
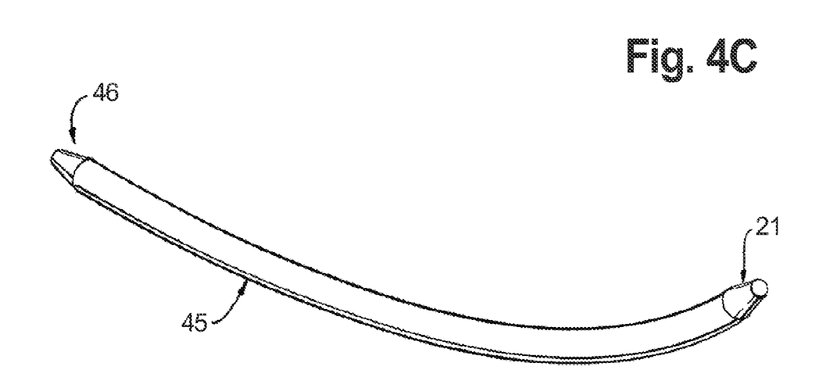
FIG. 4C is a perspective view of one particular embodiment of a rod in accordance with the principles of the present disclosure.

FIG. 4C is a perspective view of one particular embodiment of a surgical rod 21 having a marker 45 disposed on its surface (e.g., retro-reflective tape, strip, coil, etc.) that enhances the signal for tracking rod measurements in accordance with the principles of the present disclosure. The marker 45 may extend the entire length of the rod 21. In this embodiment, the marker 45 runs longitudinally on the rod to rod end 46. The tracking system may register the shape of the rod using the marker 45 along the length of the rod 21 without the need to trace a probe along the length of the surface of the rod 21. The marker 45 may be implantable with the rod 21 or may be taken off the rod 21 before implantation.

Figure 4D:
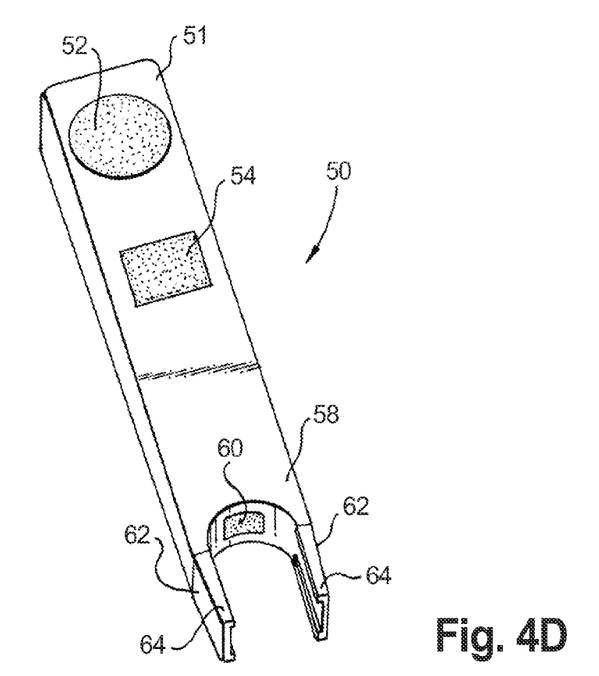
FIG. 4D is a perspective view of one particular embodiment of a probe that tracks rod measurements in accordance with the principles of the present disclosure.
Figure 5:
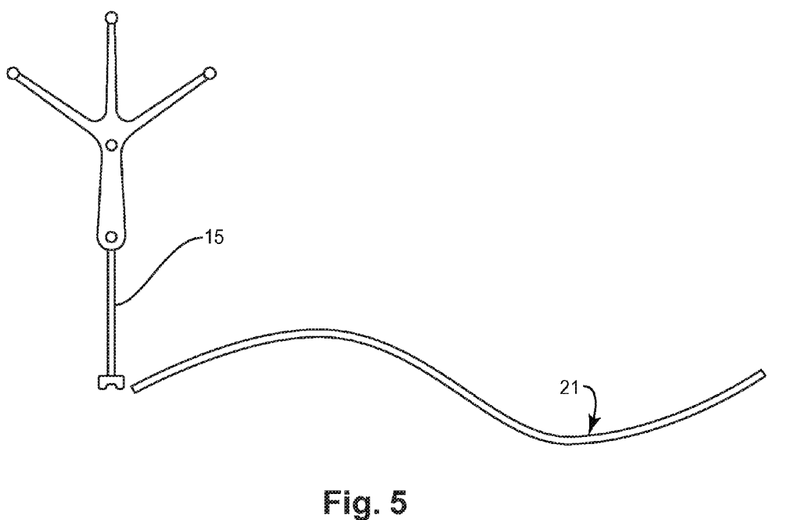
FIG. 5 is a diagram illustrating a rod and a probe in accordance with the principles of the present disclosure.
Figure 6:
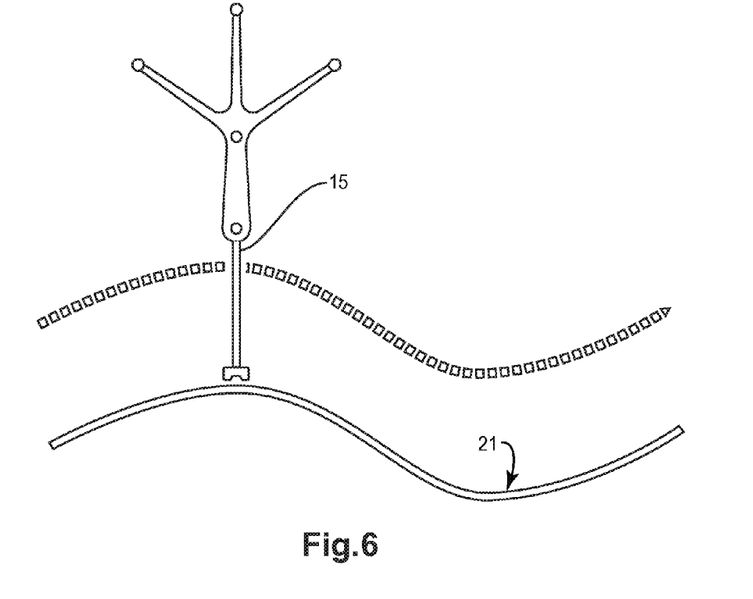
FIG. 6 is a diagram illustrating a rod and a probe moving along the rod in accordance with the principles of the present disclosure.
Figure 7:
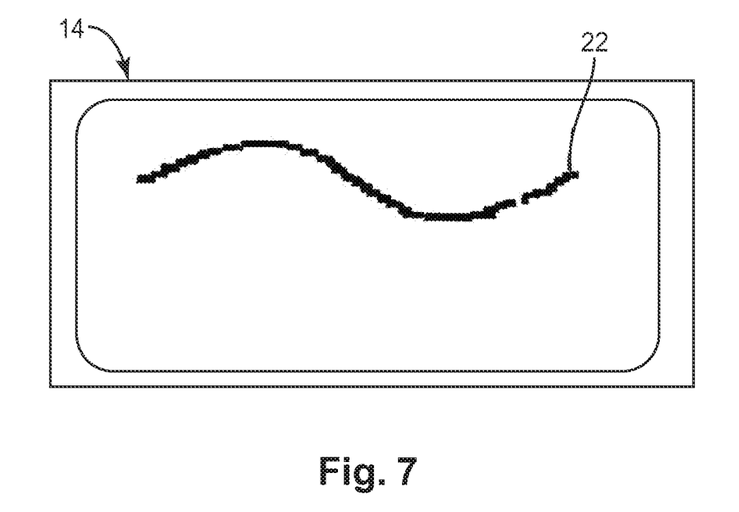
FIG. 7 is a diagram illustrating a graphical representation of the rod in accordance with the principles of the present disclosure.
Figure 8:
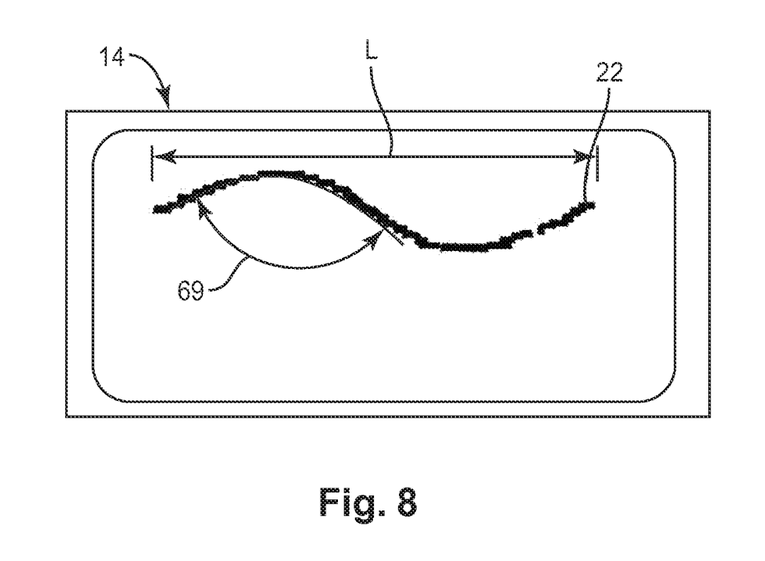
FIG. 8 is a diagram illustrating a graphical representation of the rod illustrating an angular offset in accordance with the principles of the present disclosure.

FIG. 4D is a perspective view of one particular embodiment of a probe 50 that tracks rod measurements in accordance with the principles of the present disclosure. The probe 50 comprises proximal end 51 having a control button 52 to activate the upper tracking element 54 and lower tracking element 60. At the distal end 58 of the probe 50, there are arms 62 configured to receive a rod between ends 64. In the embodiment shown, a lower tracking element 60 is disposed in the rod receiver that can be coupled to upper tracking element 54 or transmit to the computer processor (not shown). The user grips probe 50 at its proximal end 51 and traces the probe 50 longitudinally along the rod so as to obtain geometries of the rod. The probe 50 can contact the rod during the tracing or in an alternative embodiment the probe 50 can surround the circumference of the rod without contacting the rod to obtain the geometries of the rod. Arms 62 are spaced apart at a greater distance than the diameter of the rod to allow the user to trace the probe 15 along the rod. The probe 15, in some embodiments, can communicate positional and rotational information of the rod and/or probe to the processor in either a wired or wireless configuration. It is contemplated that upper tracking element 54 and/or lower tracking element 60 can directly transmit data about the geometries of the rod and/or position to the processor without the need for a sensor. In some embodiments, the upper tracking element 54 and/or lower tracking element 60 can have imaging sensors to assist in measuring rod geometries (e.g., angles, position, rotation, etc.).

The tracing methods described above can be used separately or in tandem. Additionally, the graphical representation of the rod can be viewed in one of many views such as coronal, sagittal, A-P, lateral, or rotationally as a 3D image. Lastly, because the graphical representation of the rod is in 3d coordinates, the system can automatically or as directed by a user, display any and/or all of the numeric information related to that data be it distances, angles, curves, radii, etc.

The system 10 can also include input/output devices 16 such as, for example, a keyboard, trackball, touch screen, mouse, printer, etc. The input/output devices 16 can be used to calibrate the system, position and/or rotate the graphical image 22 on the display 14, control the display 14, select points of reference on the graphical image 22, and/or perform various other functions of the system.

Figure 2:
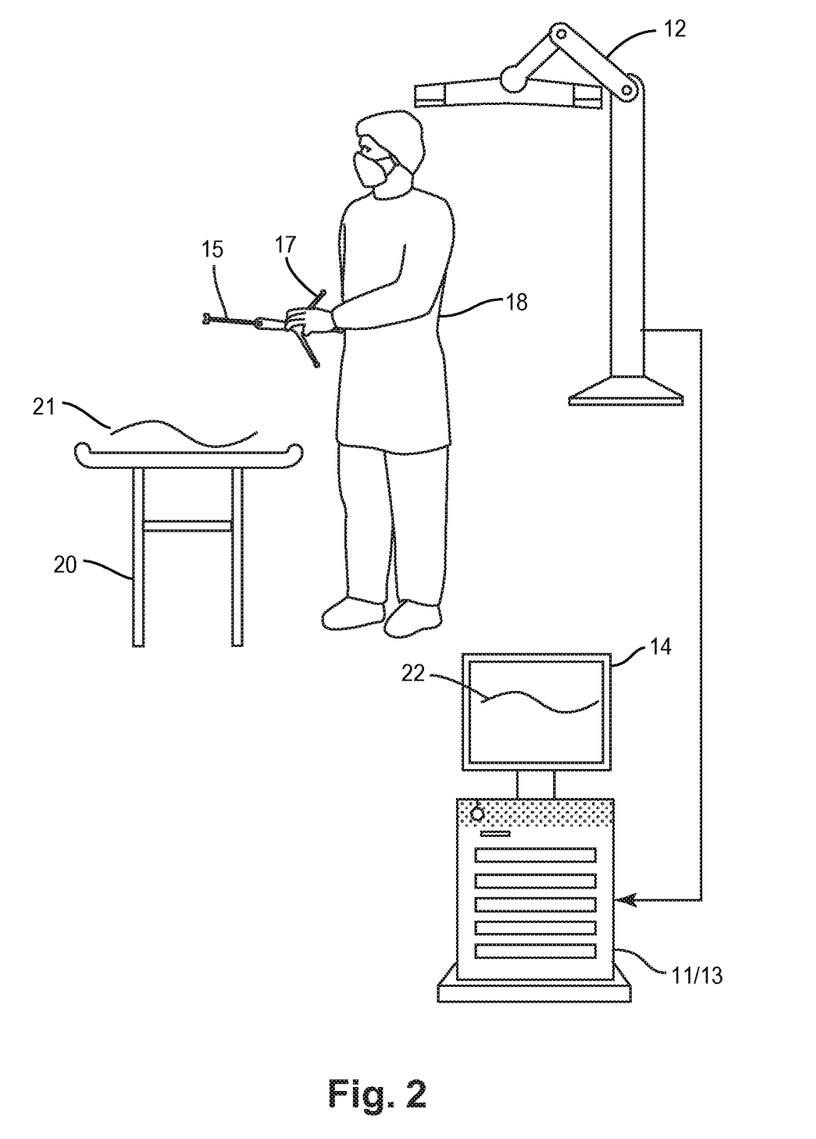
FIG. 2 is a perspective view of a system for measuring a surgical rod in accordance with the principles of the present disclosure.
Figure 3:
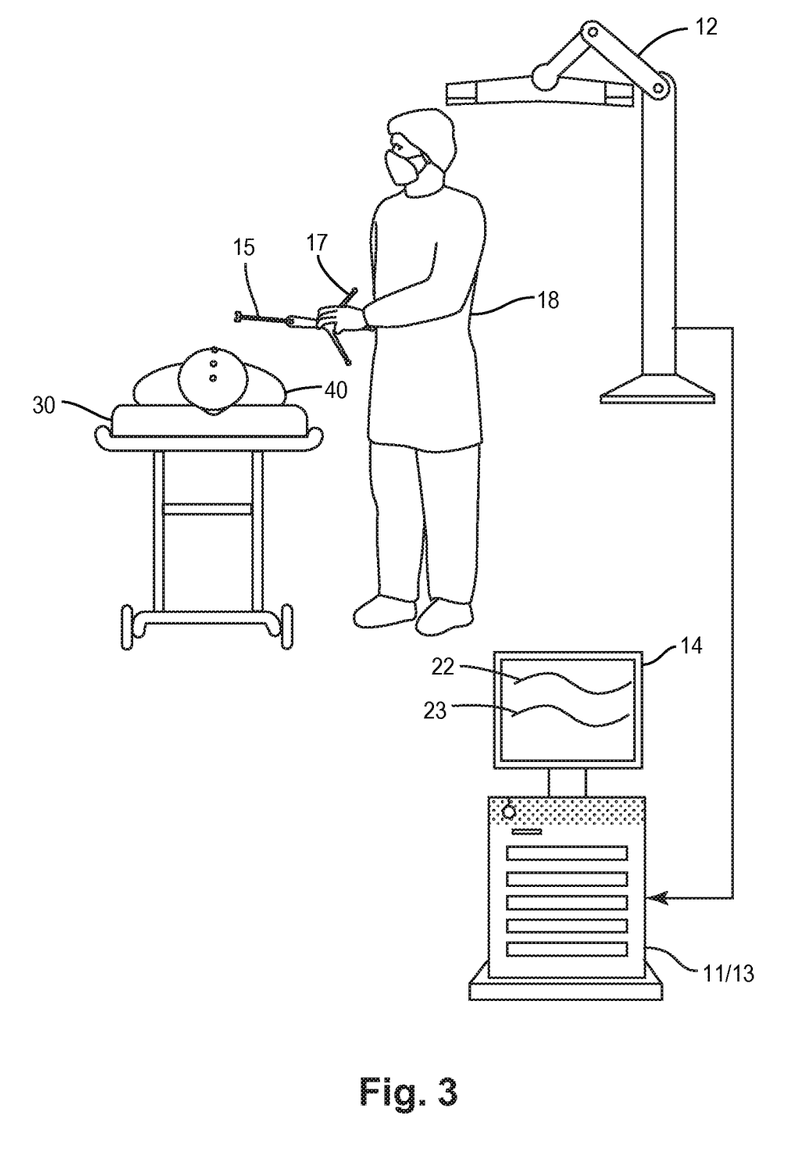
FIG. 3 is a perspective view of a system for measuring a surgical rod in accordance with the principles of the present disclosure.

As a general rule, after making the decision to implant a fixation system into a patient, a surgeon will take a plurality of spinal measurements of the patient and determine the precise geometries required for the spinal rod. That is, the surgeon determines a number of bends and angles of the bends to the rod required in the sagittal, coronal and/or transverse planes. These predetermined/preoperative measurements are brought into the operating room where the rod 21 is initially bent on a back table 20 prior to being positioned within the patient 40. The preoperative measurements can also be input into the measuring system 10 and stored in memory 13 for later use in confirming the proper bending of the rod 21, as will be described below. Once the surgeon 18 is satisfied with the bending of the rod 21, the rod 21 is taken from the back table 20 and positioned in fasteners (e.g., bone screws) 41 previously implanted into the patient 40 on the operating table 30. The surgeon 18 can again adjust the bends in the rod 21. The surgeon 18 then tightens the set screws 42 onto the rod 21 to secure the rod 21 in the fasteners (e.g., bone screws) 41. The surgeon 18 now has yet another opportunity to adjust the bends in the rod 21 before closing the patient 40. The present invention assists the surgeon in the operating room by providing the surgeon with a precise and accurate method to confirm that a rod is properly bent according to the pre-operative measurements and calculations and that the final construct remains within therapeutic limits through reduction, tightening, and/or final implantation of the rod.

In operation, the system for measuring a surgical rod 10 is located in the operating room with the surgeon 18. Initially, in step s1 the surgeon according to the pre-operative (or intra-operative) geometries determined by the surgeon bends the rod 21 on the back table 20. The bending step may include multiple bends in different planes to correct lordotic/kyphotic and scoliotic bends which may require bending the rod in sagittal, coronal, and transverse planes. At step s2, the probe 15 is placed at one end of the rod 21. (See FIG. 5). In step s3 the system is initialized, which includes determining an initial position and orientation of the probe 15. This initialization can occur by providing an input to the processor 11. Such an input can be from a touch screen, a keyboard, foot pedal or a button (not shown) on the probe 15 itself. Next, in step s4 the probe 15 is moved along the rod 21 to trace the rod 21. (See FIG. 6.) During the tracing step the processor 11 continually receives position and orientation (e.g. linear and rotational movement) data of the probe 15, and by extension the 3D coordinates of the rod. The data may be XYZ coordinates, polar coordinates, or built on some reference frame within the data. This can be started and stopped multiple times along the rod. In step s5 the processor stores the data in memory 13. In step s6 processor 11 can read the data from memory 13 and create the graphical representation 22 of rod 21 and displays on display 14 a graphical representation 22 of rod 21. (See FIG. 7.) Since the data of the tracing of the rod 21 is stored in memory 13, in step s7 processor 11 calculates the geometries 50 of the graphical representation 22 of the rod 21. That is, processor 11 determines the angles between various points on the graphical representation. (See FIG. 8.) These points can be selected automatically by the processor 11 or can be manually selected using one of the input devices 16 described above. Other characteristics of the rod 21, may also be input into the system. For example, if the surgeon would like specific radii or specific lengths for portions or all of the rod 21, then the processor 11 may receive that input and calculate the rod shape based on that input information in accordance with the data. In step s8 the actual value of the measurements can be displayed on display 14 so that the surgeon can confirm that the rod 21 has been bent according to the predetermined geometries. If it is determined in step s9 that the angles/geometries/measurements do not match the predetermined geometries the process can be repeated until the surgeon is satisfied with the results.

Since the pre-operative measurements can be stored in memory 13, processor 11 can use this pre-operative data to determine if the geometries of the rod 21 are correct by comparing the geometries of the preoperative data with the geometries of the probe data. For example, measurements between different points on the graphical representation 22 can be compared with corresponding points and angles from the preoperative geometries to determine if the measurements correspond. As with the earlier selection of points, these points can be selected automatically by the processor 11 or can be manually selected using one of the input devices 16 described above.

Figure 9:
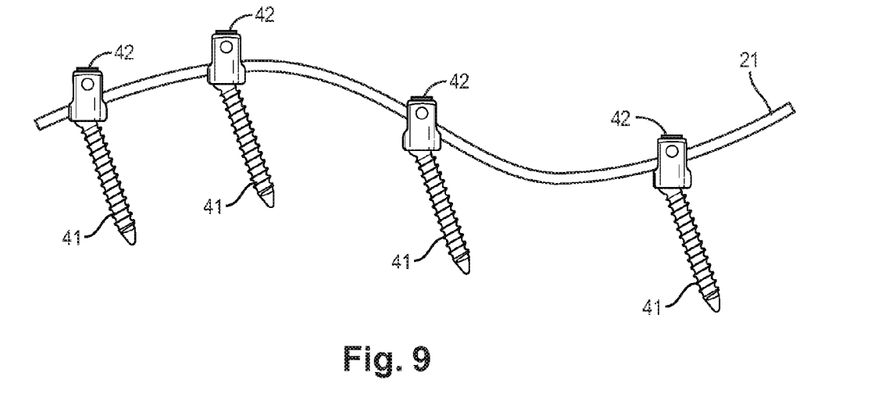
FIG. 9 is a diagram illustrating a rod positioned with bone screws in accordance with the principles of the present disclosure.
Figure 10:
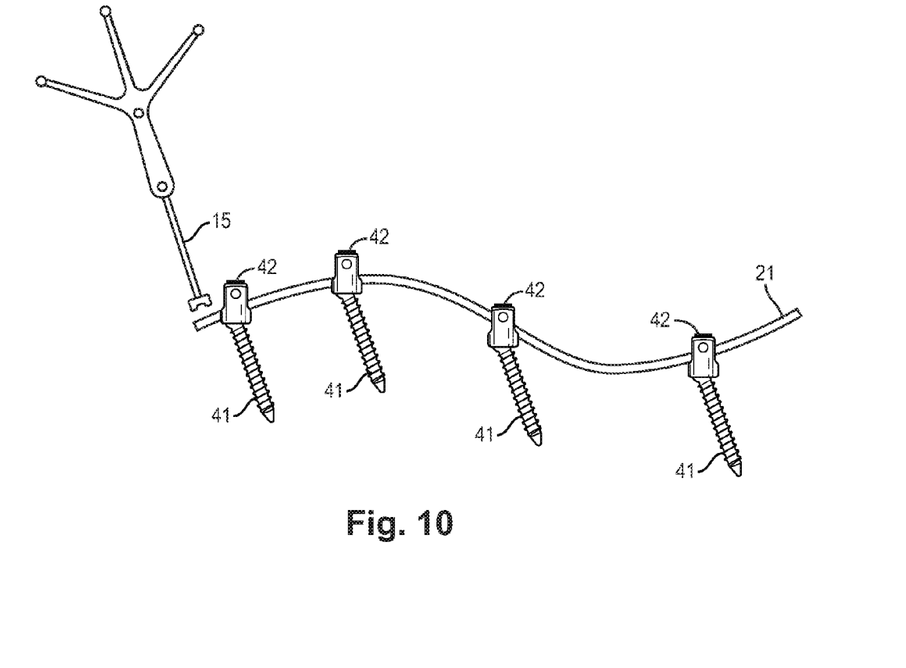
FIG. 10 is a diagram illustrating a rod positioned with bone screws and a probe in accordance with the principles of the present disclosure.
Figure 11:
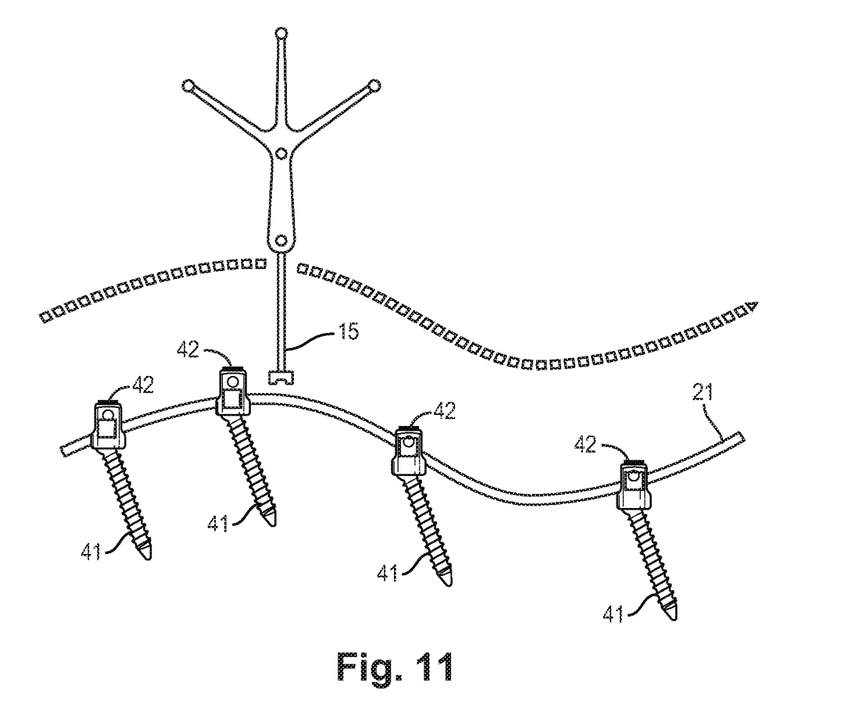
FIG. 11 is a diagram illustrating a rod positioned with bone screws and a probe moving along the rod in accordance with the principles of the present disclosure.

In step s10 the implant is positioned within the implanted fasteners (e.g., bone screws) 41 in the patient 40. In some embodiments, the fasteners 41 can include a tracking element. In an open procedure, the rod 21 may be positioned within the receivers through a large open wound. In a minimally invasive procedure, the rod 21 may be advanced through a small incision and laterally guided through the fasteners 41. The display may show the fasteners 41 based on the tracking elements on the fasteners 41. The tracking elements 41 may include extenders attached to the fasteners 41 to help urge the rod into the fasteners 41 when the rod is being guided subcutaneously. Thus, the known shape of the rod 21 can be combined with the known positions of the fasteners 41 to allow a display to show a guided path for positioning the rod 21 in the fasteners 41.

Additional bending of the rod 21 may be required at this point to properly seat the rod 21 in the fasteners (e.g., bone screws) 41. The bending may be accomplished in-situ in an open case. Once the rod 21 is seated in the fasteners 41, set screws 42 can be installed. Tightening of the set screws 42 may occur at this time or additional bending of the rod 21 can occur before the set screws 42 undergo a final tightening onto rod 21. Further, after the set screws 42 are tightened onto rod 21, the surgeon 18 can bend the rod 21 further. Various combinations of these procedures can occur until the surgeon 18 is satisfied with the geometries of the rod 21 and fixation system.

Now that the rod 21 has been secured in the fasteners (e.g., bone screws) 41, the surgeon 18 can again determine the geometries of the implanted rod 21 with the aid of the measurement system 10. That is, in step s11 the probe 15 is again placed at one end of the rod 21. (See FIG. 10). In step s12 the system is initialized to determine the initial position and orientation of the probe 15. Next, in step s13 the probe 15 is moved along the rod 21 to trace the rod 21. (See FIG. 11.) During the tracing step the processor 11 receives position and orientation (e.g. linear and rotational movement) data of the probe 15. This process is similar to that of the earlier back table tracing, but differs in that the rod 21 can only be traced along lengths between the fasteners (e.g., bone screws) 41. That is, the data obtained from the trace will have gaps 43 that represent the positions of the fasteners (e.g., bone screws) 41. Conversely, the probe can be placed through the set screws on the rod and get the inverse of FIG. 12 or do both and have almost no gaps. Standard smoothing algorithms exist that could be employed to complete the spaces and show an interpolated continuous line.

In step s14 the processor stores the data in memory 13. In step s15 processor 11 reads the data from memory 13 and creates a second graphical representation 23 of rod 21 to be displayed on display 14. (See FIG. 12.) This second graphical representation 23 represents the geometries of the rod 21 as positioned in the fasteners (e.g., bone screws) 41. The surgeon 18 can use these graphical representations 22/23 to determine if the geometries of the rod 21 are correct. They can be displayed together separately or with the pre-operation data. They can also be overlayed to visually see the differences.

Figure 12:
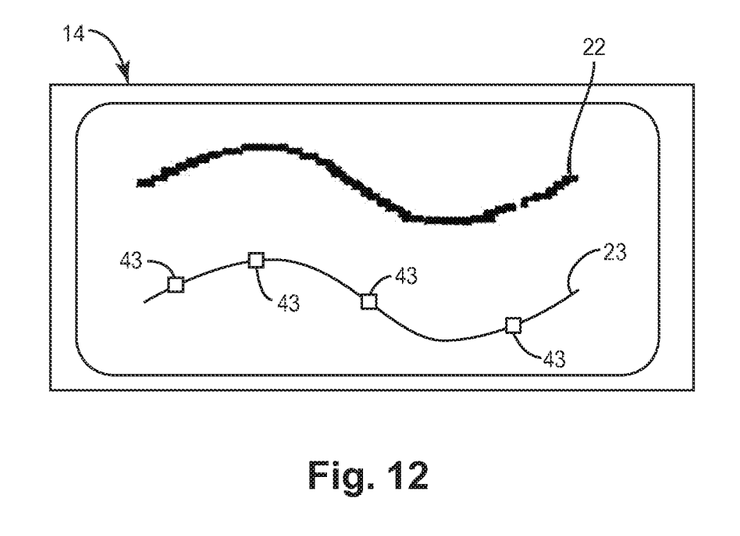
FIG. 12 is a diagram illustrating a graphical representation of rods in accordance with the principles of the present disclosure.

In step s16 processor 11 can now calculate the geometries of the graphical representation 23 of the rod 21. That is, processor 11 determines the angles between various points on the graphical representation. These points can be selected automatically by the processor 11 or can be manually selected using one of the input devices 16 described above. In step s17 the actual value of the measurements can be displayed on display 14 so that the surgeon can confirm that the rod 21 has been bent according to the predetermined geometries. If it is determined in step s18 that the angles/geometries do not match the predetermined geometries the rod 21 can be bent again in step s19 and process can be repeated until the surgeon is satisfied with the results. When the surgeon 18 is satisfied with the results, the patient can be closed and the operation completed.

In lieu of steps s11 thru s13, an imaging device such as an O-arm can be used to scan the position of the rod in the patient. Because the imaging device is also tracked with a tracker 17, the 3d position of the rod can be ascertained and displayed as above to then be manipulated and interrogated for measurement data.

As can be seen, the system and methods for measuring a surgical rod can greatly assist a surgeon during the installation of the fixation system. Further, system and methods for measuring a surgical rod can provide an accurate confirmation of the geometries of the fixation system.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A system for measuring an implant, comprising:
   a processor;
   a probe in communication with the processor and configured to trace along a surface of the implant;
   a tracking system in communication with the processor and the probe for generating first data representing at least one of linear and rotational movement of the probe during a first trace along the surface of the implant;
   wherein the processor is configured to receive the first data and generate a first graphical representation of the implant based on the first data; and
   a display in communication with said processor for displaying the first graphical representation of the implant based on the first data,
   wherein the processor is configured to calculate an angular offset between at least two portions of the implant based on the first data and display the angular offset.

2. The system of claim 1, wherein the processor is further configured to calculate based on the first data a measurement between the at least two portions of the implant and display the measurement, wherein the measurement is at least one of a linear length, a radius and a curve.

3. The system of claim 1, wherein the processor is further configured to receive second data from a second tracing of the implant by the probe, generate a second graphical representation of the implant based on the second data, and display on the display the second graphical representation of the implant based on the second data.

4. The system of claim 1, wherein the tracing is non-contiguous.

5. The system of claim 1, wherein the implant is a surgical rod that is bent according to a surgical plan dependent on a patient's anatomy.

6. The system of claim 1, wherein the first data is three dimensional data and the first graphical representation is a three dimensional representation of the implant.

7. The system of claim 1, wherein said tracking system is an optical tracking system.

8. The system of claim 1, wherein the tracking system comprises an active tracking system that includes a gyroscope for determining rotational movement of the probe.

9. The system of claim 1, wherein the tracking system comprises an active tracking system that includes an accelerometer for determining linear movement of the probe.

10. The system of claim 1, wherein:
    the probe comprises a pair of spaced apart arms that define an implant cavity therebetween, the probe comprising a tracking element that is in communication with the implant cavity; and
    the implant is positioned within the implant cavity as the probe traces along the surface of the implant.

11. The system of claim 1, wherein the implant is positioned within an implant cavity of the probe as the probe traces along the surface of the implant, the implant cavity comprising a tracking element configured to communicate positional and rotational data about the implant to the processor.

12. A method for measuring an implant, comprising:
    moving a probe along a surface of the implant prior to positioning the implant within a patient, the implant being positioned within an implant cavity of the probe as the probe moves along the surface of the implant, the implant cavity comprising a tracking element configured to communicate positional and rotational data about the implant;
    tracking by a tracking system movement of the probe to obtain first data representing the implant;
    storing the first data in a memory;
    displaying on a display a first image representing the implant based on the first data;
    calculating by a processor based on the first data angular offsets between at least two points of the implant; and
    displaying the angular offsets.

13. The method of claim 12, further comprising:
    modifying at least one geometry of the implant;
    moving the probe along the surface of the implant;
    tracking movement of the probe to obtain second data representing the implant;
    storing the second data in the memory;
    displaying a second image representing the implant based on the second data;
    recalculating angular offsets based on the second data; and
    displaying the recalculated angular offsets.

14. The method of claim 12, further comprising:
    modifying at least one geometry of the implant;
    moving the probe along a surface of the implant;
    tracking movement of the probe to obtain second data representing the implant;
    storing the second data in the memory; and
    displaying a second image representing the implant based on the second data.

15. The method of claim 12, further comprising:
positioning the implant in the patient;
connecting the implant to anchors positioned in the patient;
moving the probe along the surface of the implant;
tracking movement of the probe to obtain second data of the implant within the patient;
storing the second data in the memory; and
displaying a second image representing the implant based on the second data.

16. The method of claim 15, further comprising:
comparing the first and second images;
modifying at least one geometry of the implant;
moving the probe along the surface of the implant;
tracking movement of the probe to obtain third data representing the implant;
storing the third data in the memory; and
displaying a third image representing the implant based on the third data.

17. The method of claim 12, further comprising the steps of:
tracking a position of the implant;
tracking a fastener relative to the implant position;
displaying the fastener on the display relative to the implant; and
guiding the implant toward the fastener using the display to show the relative position of the fastener to the implant.

18. A method for measuring a surgical rod, comprising:
inserting at least one bone fixation element into a patient;
bending the rod prior to positioning the rod within the patient;
capturing first data using a probe to represent a shape of the rod after the bending step;
storing the first data in a memory;
displaying a first image representing the rod based on the first data;
positioning the rod in the patient;
connecting the rod to the at least one bone fixation element;
capturing second data using the probe to represent the shape of the rod after the positioning step;
storing the second data in the memory; and
displaying a second image representing the rod based on the second data.

19. The method of claim 18, further comprising:
comparing the first and second images;
modifying at least one geometry of the rod;
moving the probe along a surface of the rod;
tracking movement of the probe to obtain third data representing the rod;
storing the third data in the memory; and
displaying a third image representing the implant based on the third data.

\* \* \* \* \*